United States Patent [19]

Figallo E.

[11] 4,153,053
[45] May 8, 1979

[54] METHOD OF REDUCING MALAR FRACTURES USING A HAMMER DISIMPACTOR

[76] Inventor: Eleazar Figallo E., Clinica El Avila Altamira, Caracas, Venezuela

[21] Appl. No.: 832,624

[22] Filed: Sep. 12, 1977

[51] Int. Cl.² ........................ A61B 17/18; A61F 5/04
[52] U.S. Cl. .............................. 128/92 E; 128/92 EC; 128/303 R
[58] Field of Search .............. 128/92 E, 92 EC, 92 R, 128/303 R, 83, 89 A

[56] References Cited

U.S. PATENT DOCUMENTS 2,121,193   6/1938   Hanicke ........................ 128/92 EC

OTHER PUBLICATIONS

McReynolds Driver-Extractor Instrument (No. 6869), Vitallium Surgical Appliances (Catalog), Austenal Medical Div., Howmet Corp., N.Y., N.Y., p. 76, 1964.
Drill–Guide Instrument (21-1200), Orthopedic Catalog, Richards Mfg. Co., Inc., Memphis, Tenn., 1974, p. 43.
Kuntscher Nail Extractor (11-0190), Orthopedic Catalog, Richards Mfg. Co., Inc., Memphis, Tenn., 1974, p. 112.
Richards Mfg. Co. (Catalog), Memphis, Tenn., Driver-Extractor (No. 956 DE), 1966, p. 82.

*Primary Examiner*—Ronald L. Frinks
*Attorney, Agent, or Firm*—Browdy and Neimark

[57] ABSTRACT

A device to reduce or set malar fractures, which does not depend on the strength of the operator, comprises a stainless steel rod with a hook on one end, a handle on the other end, a movable hammer which slides freely along the rod and two stops for the hammer, one at each end of the rod. The hook is inserted under the lower edge of the malar. The force required for separating the impacted bones is produced when the hammer hits the main stop built into the rod at the end opposite the hook, stops suddenly, thereby producing a force on the hook. Since the hook is in contact with the impacted bone, the force is communicated to the bone.

3 Claims, 5 Drawing Figures

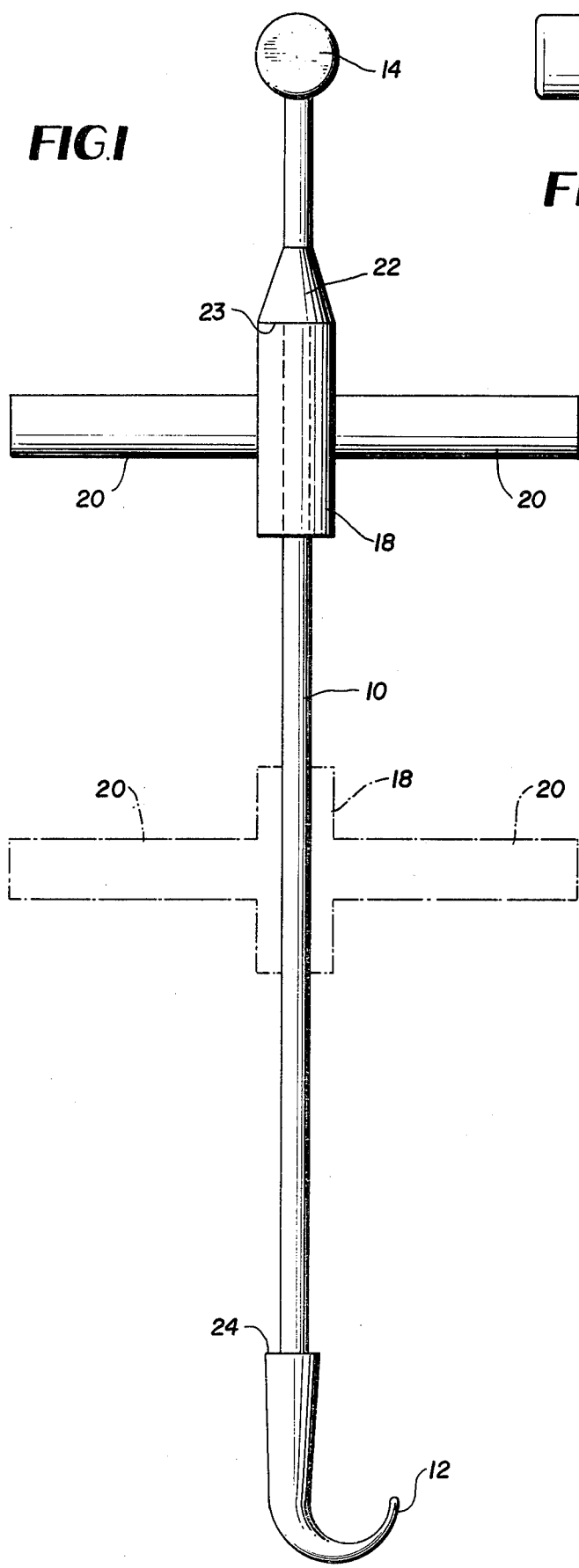
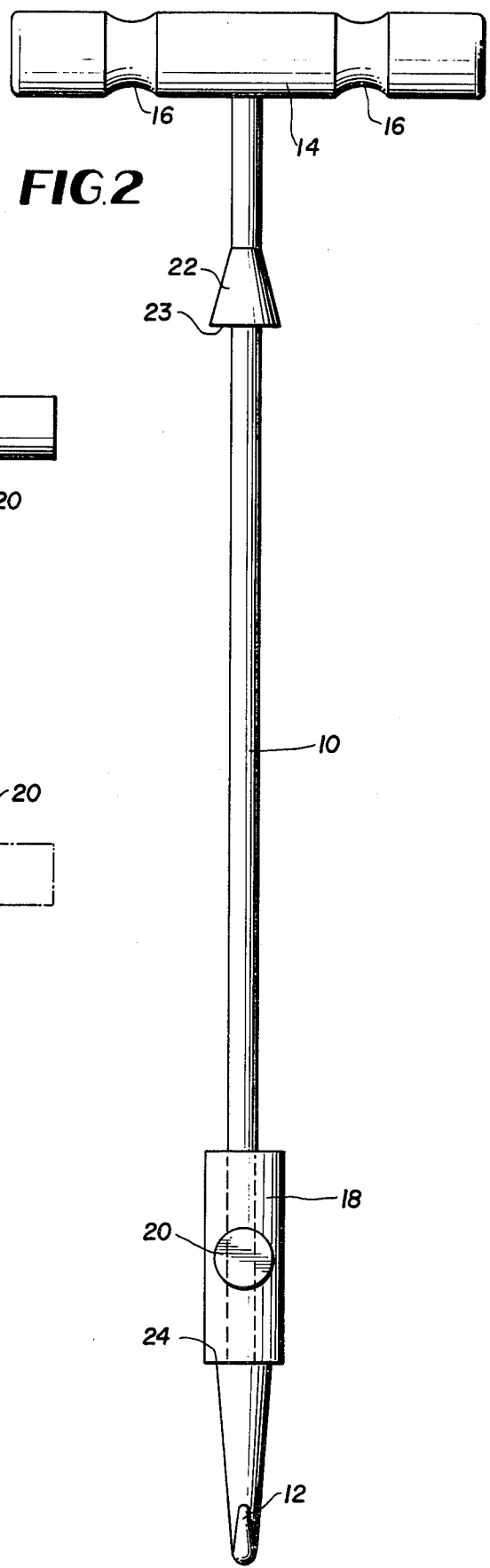

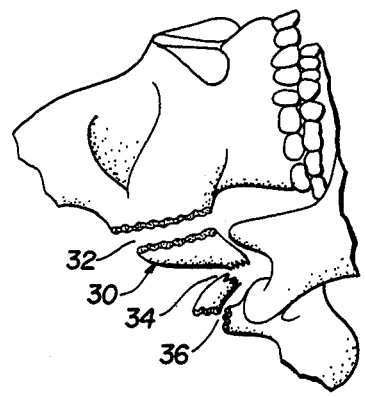
FIG.3
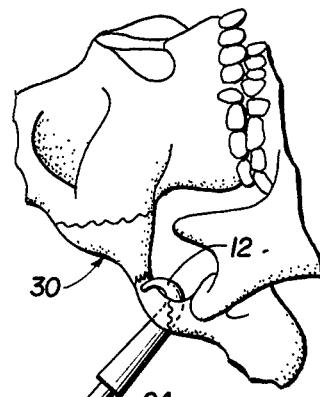
FIG.4
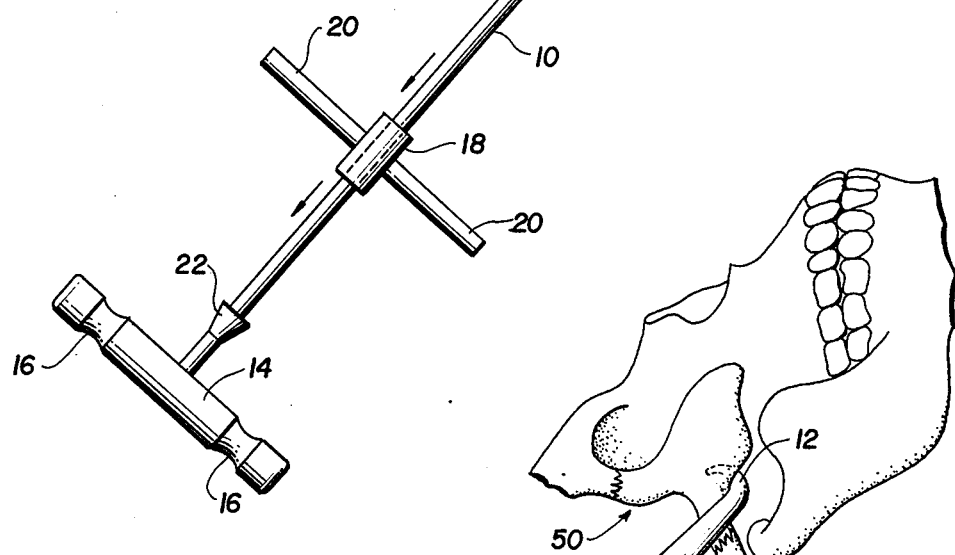
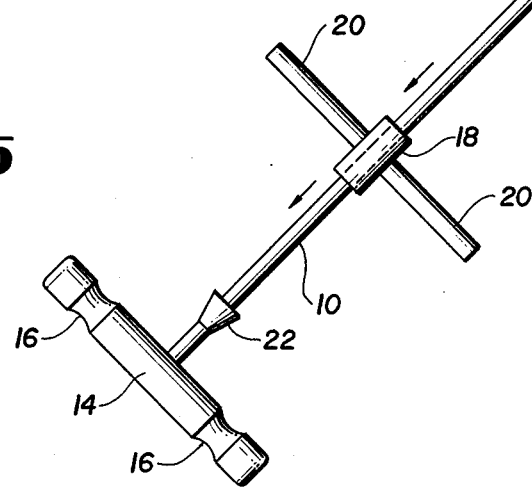
FIG.5

4,153,053

METHOD OF REDUCING MALAR FRACTURES USING A HAMMER DISIMPACTOR

FIELD OF THE INVENTION

The invention relates to the repair of fractures and, more particularly, to a device and a method to reduce, i.e., repair or set, malar fractures.

BACKGROUND OF THE INVENTION

The malar, due to its prominent position, is often fractured, either alone or jointly with other bones in the middle of the facial area. Because the body of the malar is relatively strong compared to its processes, it is these processes which are frequently fractured. In the simple fracture-luxation, the zygomatic bone is separated from its union with the frontal bone, the sphenoid bone, the zygomatic arch, and the maxilla; the malar is displaced downward, into the face, and thus the external border is broken. In serious lesions diplopia, other ocular disturbances, and a deterioration of the mandibular function can occur.

Traditional methods of setting the fractured malar use levers or bone hooks. The best known procedure is that of Gillies. It consists of a temporal incision and the introduction of an elevating lever under the aponeurosis of the temporal muscle. Once one end of the lever has reached the fracture, a reduction is attempted by supporting the lever against the bones of the head. Other vias such as the Caldwell-Luc via, and the supraorbital via, and other instruments such as bone hooks, can also be used to lift the sunken bone. All known procedures to date depend upon the strength of the operator.

Most researchers agree that fractures of the zygomatic bone, when seen within the first few days after the lesion, can still be treated satisfactorily by simple methods of elevation. The zygomatic bone generally maintains satisfactory position after the reduction or setting, since the irregular borders of the bony fragments help the bones interlock during the reduction, and since no strong muscular traction exists which could dislocate the acquired position.

Fractures of the zygomatic bone often remain undetected because the soft, tumefactious tissue often hides the depressed parts. Fractures of the malar which remain for a considerable period of time without treatment may undergo a great deal of displacement, may become impacted, or may become partially consolidated. These complications cannot be adequately treated with traditional methods. For this reason means other than those heretofore available are necessary.

SUMMARY OF THE INVENTION

It is, accordingly, an object of the invention to overcome deficiencies in the prior art, such as those indicated above.

It is a further object to provide for improved repair of bone fractures.

Yet another object is the provision of an improved instrument for the setting of malar fractures.

Another object of the present invention is the reduction of malar fractures which have undergone a large amount of displacement.

A further object of the present invention is the reduction of malar fractures which are impacted.

Another object of the present invention is the reduction of malar fractures which are partially consolidated.

The apparatus which achieves these goals consists of a metal rod with a hook on one end, a movable hammer which slides freely up and down the rod, and two impediments or stops on either end of the rod. The point of the hook is inserted under the lower edge of the malar. The force required for separating the impacted or displaced bone is produced when the hammer hits the impediment at the end of the rod opposite the hook, i.e., the main stop; the hammer stops suddenly, producing a force on the hook. It is this force which raises the sunken bone.

BRIEF DESCRIPTION OF THE DRAWING

For a better understanding of the invention, possible embodiments thereof will now be described with reference to the attached drawings, it being understood that these embodiments are to be intended as merely exemplary and in no way limitative.

FIG. 1 is a side view of the hammer disimpactor of the present invention.

FIG. 2 is a view of the handle at 90° from the view in FIG. 1.

FIG. 3 is a view of a fractured zygomatic arch.

FIG. 4 is a view of the hammer disimpactor of the present invention as it might be used in reducing a fracture of the zygomatic arch. The hammer moves in the direction of the arrows.

FIG. 5 is a view of the present invention as it might be used in reducing a fracture of the malar. The hammer moves in the direction of the arrows.

DETAILED DESCRIPTION OF THE PREFERRED EMBODIMENTS

The preferred embodiment, preferably made of stainless steel, comprises a rod 10 having at one end a hook 12, and at the other end a handle 14 with indentations 16 for achieving a good grip. Attached to the rod 10 so that it can slide freely thereon is a cylindrical mass 18. Attached to the movable cylinder 18 are two other appurtenances 20. The cylindrical mass and its two appurtenances together form a hammer. These two appurtenances 20 allow one to more easily grasp the cylindrical mass 18.

Two impediments or stops 22, 24 on the rod 10 are provided to stop the freely moving mass. They are attached to the rod 10 so that the hammer 18, 20 does not slip off at either end and so that the hammer 18, 20 stops suddenly, producing a force of disimpaction. The barrier near the handle 14, the main stop, consists of a truncated cone 22 which envelops the rod 10 such that the base 23 of the cone 22, which is wider than the diameter of the rod 10, faces the hook 12. The other stop 24 comprises the end portion of the hook 12 which attached to the rod 10, said portion of the hook 12 is also in the shape of a cone, such that the face of portion 24, which is larger in diameter than the rod 10, faces the handle end of the rod 10.

Of course, the stops described above may be produced in a variety of shapes and can be placed anywhere along the rod.

FIG. 3 is a schematic view of a portion of the skull. The zygomatic arch 30 as shown is broken at 34, 32 and 36.

The instrument can be used in the following manner: A small incision in the skin is made with a scalpel or other suitable knife-blade. The point of the hook 12 is introduced into the incision, positioned under the lower edge of the zygomatic arch 30 or the malar 50, and secured against the internal face of the bone as may be seen in FIGS. 4 & 5. At this point the handle end of the rod 12, is elevated above the hooked end 14. The handle end of the rod 10 is taken in the left hand, and the mass 18 is taken between the index and middle fingers of the right hand. The mass is now placed somwhere along the rod and pushed up the rod toward the main stop with the right hand. When it reaches the impediment 22, the mass 18 stops suddenly, thereby producing a force of disimpaction on the hook 12 and therefore on the bone 30 or 50. If more force is desired, the right hand can grip the mass 18 and push it up the rod 10 with greater force.

FIGS. 4 and 5 show the invention in actual use. In FIG. 4 the hook 12 engages the zygomatic arch 30. In FIG. 5 the hook 12 engages the malar bone 50. The hammer moves in the direction indicated by the arrows. When the hammer 18 reaches the main stop 22, its motion is suddenly halted, and the resulting force pulls the hook 12 and the bone to which saidhook 12 is attached, in the direction of the arrows.

It will be obvious to those skilled in the art that various changes may be made without departing from the scope of the invention and the invention is not to be considered limited to what is shown in the drawings and described in the specification.

It should be understood that the terms "malar" and "malar fracture", as used in the present specification and claims, refers not only to fracture of the malar (or zygomatic) bone, but also to the zygomatic arch, and other bones in the facial area. What is claimed is:

1. A method of reducing malar fractures using an instrument comprising a rod, a hook attached to one end of said rod, a mass slidably engaging said rod, and main stopping means connected to said rod between said mass and the end of said rod opposite said hook, for stopping said mass when said mass is sliding on said rod in the direction away from said hook, said method comprising the steps of:
    (a) making an incision in the skin in the vicinity of the fractured malar;
    (b) inserting the point of the hook of said instrument into the incision and positioning said hook so that said hook is under the lower edge of the malar;
    (c) securing said hook against the internal face of the malar;
    (d) causing said mass to slide on said rod and impact said main stopping means, whereby the force is transmitted to the bone producing a force of disimpaction thereon; and
    (e) unhooking the instrument from the malar and removing the instrument from the incision.

2. A method of reducing malar fractures according to claim 1, wherein said instrument is so positioned after said step (c) that said main stopping means is elevated higher than said hook.

3. A method of reducing malar fractures according to claim 2 wherein said step (d) comprises pushing said mass up the rod toward said main stopping means.

* * * * *